(12) United States Patent
Lee et al.

(10) Patent No.: US 8,251,206 B2
(45) Date of Patent: Aug. 28, 2012

(54) PASTE COMPOSITION STORAGE DEVICE AND METHOD

(75) Inventors: Robert Lee, Lake Elmo, MN (US); Marc Peuker, Schondorf (DE); Arno Hohmann, Munich (DE); John W. Dubbe, Starnberg (DE); Tomas L. Fridinger, White Bear Lake, MN (US)

(73) Assignee: 3M Innovative Properties Company, Saint Paul, MN (US)

( * ) Notice: Subject to any disclaimer, the term of this patent is extended or adjusted under 35 U.S.C. 154(b) by 2144 days.

(21) Appl. No.: 10/890,748

(22) Filed: Jul. 14, 2004

(65) Prior Publication Data

US 2005/0205452 A1 Sep. 22, 2005

Related U.S. Application Data

(60) Provisional application No. 60/487,359, filed on Jul. 15, 2003.

(51) Int. Cl.
*A61B 19/02* (2006.01)
*B65D 25/08* (2006.01)

(52) U.S. Cl. ............. 206/63.5; 206/219; 206/820

(58) Field of Classification Search .............. 206/368, 206/219, 220, 221, 538, 534, 459.5, 820, 206/484, 63.5
See application file for complete search history.

(56) References Cited

U.S. PATENT DOCUMENTS

| 3,722,833 | A | | 3/1973 | Inoue et al. |
| 5,613,609 | A | * | 3/1997 | Hamilton et al. ............. 206/531 |
| 5,660,273 | A | | 8/1997 | Discko, Jr. |
| 5,791,478 | A | * | 8/1998 | Kalvelage et al. ............ 206/531 |
| 5,928,213 | A | | 7/1999 | Barney et al. |
| 6,105,761 | A | | 8/2000 | Peuker et al. |
| 2002/0122685 | A1 | | 9/2002 | Lee et al. |
| 2004/0029077 | A1 | * | 2/2004 | Peuker et al. ............. 433/217.1 |

FOREIGN PATENT DOCUMENTS

| DE | 19906565 A1 | 8/2000 |
| DE | 100 47 679 | 4/2002 |
| EP | 0 916 593 | 5/1999 |
| EP | 1 216 933 | 6/2002 |
| WO | WO 99/59874 | 11/1999 |
| WO | WO 01/64544 A1 | 9/2001 |
| WO | WO 01/64547 A1 | 9/2001 |
| WO | WO 01/85569 A1 | 11/2001 |
| WO | WO 02/38465 A2 | 5/2002 |
| WO | WO 02/38465 A3 | 5/2002 |

* cited by examiner

*Primary Examiner* — J. Gregory Pickett
(74) *Attorney, Agent, or Firm* — Peter L. Olson; Eloise J. Maki (57) ABSTRACT

A device for storing and mixing a plurality of paste components which, when mixed, form a hardenable composition, includes a base plate and a cover. The base plate has an upper planar surface bearing two or more non-self-leveling pastes and adhered thereon in spaced apart areas and. The cover is adhered to the upper surface of the base plate around the pastes and defines a chamber for the pastes. No portion of the cover contacts the pastes. The cover is removably affixed to the base plate, to allow exposure of the pastes for mixing together on the upper surface of the base plate.

20 Claims, 4 Drawing Sheets

PASTE COMPOSITION STORAGE DEVICE AND METHOD

CROSS-REFERENCE TO RELATED APPLICATION

This application claims priority to U.S. Provisional Patent Application No. 60/487359, filed Jul. 15, 2003

BACKGROUND OF THE INVENTION

The invention relates to a delivery device for packaging and mixing dental paste components useful for forming a hardenable dental composition. The invention also relates to creating a hardenable dental composition and the formation of a package assembly therefor. The invention is particularly adapted for dental paste components which have non-self-leveling material properties.

In connection with the preparation of dental filling and restorative materials, it is often necessary to mix two or more materials together to define a final, useful composition capable of undergoing a hardening reaction. The ratio of the mixture of materials is often critical in order to define the proper characteristics for the final composition. In the dental field, such materials may be used to prepare a hardened composition for a variety of dental restorative applications.

It is known to prepare such compositions by providing the materials in bulk and then measuring out defined amounts for combination, with subsequent mixing. Such materials may be in powdered, paste or liquid form, and the final mixture may be the result of mixing two or more of such materials. One current technique for combination is to manually transfer materials with a spoon and dropper from bulk containers and then dispense and measure out the correct ratio of materials onto a mixing pad for mixing. Alternatively, unit dose delivery methods such as capsules for mixing powders and liquids are known. However, such unit dose delivery methods require several steps including activation, and a mechanical mixing device which takes up space, is expensive and is not readily portable. In addition, reliance on the user to measure amounts of the required base materials may lead to error in preparing the mix ratio of such materials, and the use of containers or carriers in the process may, even if the appropriate amount of material is measured out, leave residue amounts of such material on those containers or carriers as the material is transferred during the dispensing and mixing process, thereby adversely affecting the appropriate mix ratio of materials. Such materials are often expensive and thus such waste is costly.

BRIEF SUMMARY OF THE INVENTION

In one form, the invention is a device for storing and mixing a plurality of paste components. The device comprises a base plate having an upper paste mixing surface and a lower surface. The upper mixing surface is planar and has first and second spaced apart paste holding areas thereon. A first non-self-leveling paste is adhered on the first paste holding area of the upper mixing surface. A first cover extends over the first paste area in non-contact relation to the first paste, with the first cover removably hermetically sealed to the upper mixing surface around the first paste. A second non-self-leveling paste is adhered on the second paste holding area of the upper mixing surface. A second cover extends over the second paste area in non-contact relation to the second paste, with the second cover removably hermetically sealed to the upper mixing surface around the second paste.

In another form, the invention is a method of creating a hardenable composition comprising providing a first paste having a first volume, with the first paste having non-self-leveling material properties, being adhered to a planar first paste area on a support surface, and protected by a first overlying cover which is hermetically sealed to the support surface around the first paste and spaced apart from the first paste. The method further comprises providing a second paste having a second volume wherein the second volume is defined as a function of the first volume, with the second paste having non-self-leveling material properties, being adhered to a planar second paste area on the support surface which is coplanar and spaced apart from the first paste area, and protected by a second overlying cover which is hermetically sealed to the support surface around the second paste and spaced apart from the second paste. The method also comprises removing the first and second covers from the support surface to expose the first and second pastes, and mixing the first and second pastes together on a planar mix area on the support surface which is coplanar with the first and second paste areas.

In another form, the present invention is a method of creating a hardenable composition comprising providing a first paste having a first volume, wherein the first paste has non-self-leveling material properties and is adhered to a planar first paste area on a support surface. The method also comprises providing a second paste having a second volume, wherein the second volume is defined as a function of the first volume of the first paste, and wherein the second paste has non-self-leveling material properties and is adhered to a planar second paste area on the support surface which is coplanar with and spaced apart from the first paste area. Also provided is an overlying cover which is hermetically sealed to the support surface about the first and second pastes and extends protectively over and is spaced apart from the first and second pastes. The method also comprises removing the cover from the support surface to expose the first and second pastes, and mixing the first and second pastes together on a planar mix area on the support surface which is coplanar with the first and second paste areas.

In another form, the invention comprises a method of forming a packaging assembly for storing and dispensing a hardenable composition formed from a combination of at least two pastes. The method comprises providing a base having a planar support surface, disposing a first paste on a first area of the support surface wherein the paste is non-self-leveling, has a base side adhered to the support surface and has one or more exposed sides, and disposing a second paste on a second area of the support surface which is spaced apart from the first area wherein the second paste is non-self-leveling, has a base side adhered to the support surface and has one or more exposed sides. The method further comprises releasably adhering a protective cover having a bottom surface and a top surface over the first and second pastes, with the bottom surface of the cover being hermetically sealed to the support surface of the base around and between each of the pastes, and with those portions of the bottom surface of the cover which extend over the first and second areas being spaced apart from the exposed sides of the respective first and second pastes disposed thereon.

While the above-identified figures set forth several embodiments of the invention, other embodiments are also contemplated, as noted in the discussion. In all cases, this disclosure presents the invention by way of representation and not limitation. It should be understood that numerous other modifications and embodiments can be devised by those skilled in the art which fall within the scope and spirit of the principals of this invention. The figures may not be drawn to scale. Like reference numbers have been used throughout the figures to denote like parts.

DETAILED DESCRIPTION

Figure 1:
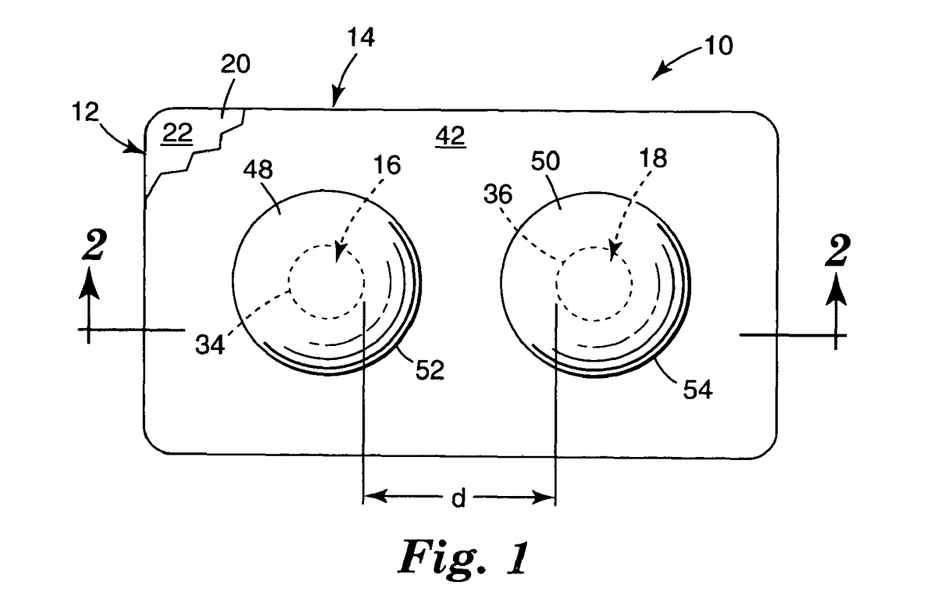
FIG. 1 is a top plan view of a delivery device for storing and mixing a plurality of dental paste components, with a corner portion of a top cover layer broken away.
Figure 2:
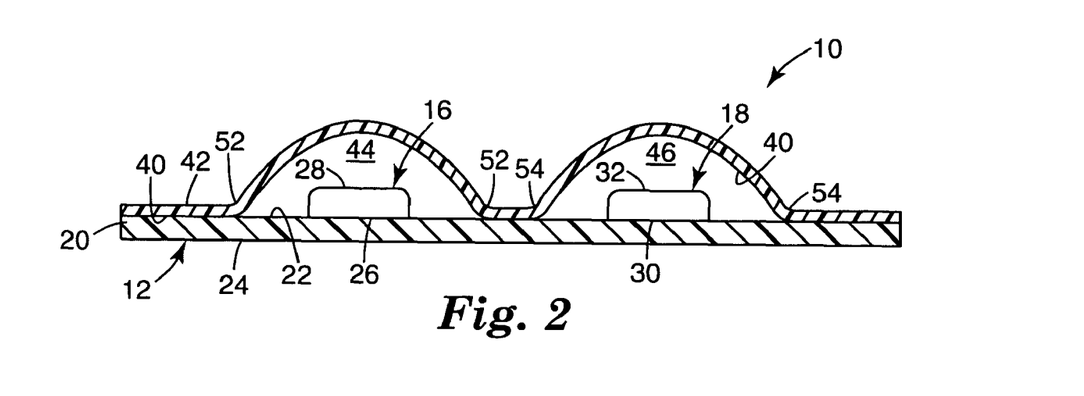
FIG. 2 is a sectional view as taken along lines 2-2 in FIG. 1.

A delivery device 10 for storing and mixing a plurality of dental paste components is illustrated in FIGS. 1 and 2. The delivery device 10 includes a base 12 and a cover 14 which cooperate to define a storage assembly for a plurality of dental pastes 16 and 18.

The base 12 in one embodiment comprises a base plate 20 having an upper surface 22 and a lower surface 24. The dental pastes 16 and 18, as seen in FIGS. 1 and 2, are a first paste 16 and a second paste 18, supported on and adhered to the upper surface 22 of the base plate 20. The first and second pastes 16 and 18 are stable paste materials which, once deposited onto the upper surface 22 of the base plate 20, do not move and retain their shape (e.g., formed as a disc or dome-shaped mass of paste on the base plate 20). The first paste 16 has a base side 26 affixed to the upper surface 22 and one or more exposed sides 28, and the second paste 18 likewise has a base side 30 affixed to the upper surface 22 and one or more exposed sides 32. The upper surface 22 of the base plate 20 has a paste area for receiving each of the pastes. Accordingly, the base side 26 of the first paste 16 is disposed on a first paste holding area 34 while the base side 30 of the second paste 18 is disposed on a second paste holding area 36 (see FIG. 1). The first paste area 34 and second paste area 36 are spaced apart (such as by a defined distance d, as illustrated in FIG. 1). The first and second paste areas 34 and 36 are generally planar, and are coplanar with one another. The upper surface 22 of the base plate 20 is also generally planar and serves to define a mixing surface for the pastes 16 and 18 when a hardenable dental composition is to be prepared. The upper surface 22 is smooth, or may be provided with a desired texture such as a microreplicated surface in order to enhance the adherence of the paste or the mixing of the paste materials together. The base 12 may have one or more handles or textured portions to facilitate handling.

The cover 14 extends over the upper surface 22 of the base plate 20 and the first and second pastes 16 and 18 thereon. The cover 14 has a bottom surface 40 and a top surface 42. The bottom surface 40 of the cover 14 is releasably and hermetically sealed to the upper surface 22 of the base plate 20 around the first and second pastes 16 and 18. The cover 14, while having some rigidity, is also flexible enough to be peeled off of the base plate 20 for exposure of the pastes 16 and 18 thereunder. The cover 14 is formed, in one embodiment, as a continuous layer of cover material which defines an enclosure or chamber for the pastes 16 and 18, in combination with the upper surface 22 of the base plate 20. In the embodiment shown in FIGS. 1 and 2, each paste has its own respective chamber: a first chamber 44 for first paste 16 and a second chamber 46 for second paste 18. The chambers 44 and 46 may be dome shaped as shown, or may take any other suitable shape for protectively covering the pastes thereunder. No matter what form the chamber takes for its respective paste, the bottom surface 40 of the cover 14 is spaced apart from any of the exposed sides of that paste (i.e., in a non-contacting, spaced apart relationship). Thus, each paste 16 or 18 is only in contact with the upper surface 22 of the base plate 20, and does not contact the bottom surface of the cover 14.

Each chamber 44 and 46 also defines a specific interior volume therein. Thus, for example, chamber 44 has an interior volume defined by the volume of the paste 16 and the remaining volume of the chamber 44. The remaining volume may simply be constituted as air or may be evacuated to form a vacuum within. The remaining volume (and gas, if any, disposed therein) may be selected as a function of the composition and volume of the paste within that chamber.

To form the chambers 44 and 46, the cover 14 may be shaped to have one or more raised areas or dome portions 48 and 50 thereon. In the embodiment illustrated in FIGS. 1 and 2, the bottom surface 40 of the cover 14 is sealed to the upper surface 22 of the base plate 20 not only around the first and second pastes 16 and 18, but also between the pastes 16 and 18, thus forming a separate hermetically sealed chamber 44 and 46 for each of the pastes 16 and 18, respectively. The cover 14 and base plate 20 are sealed together at least along seal lines 52 and 54. While a two-paste mixture is illustrated, mixtures involving three or more paste components are contemplated. In that instance, each paste component may be provided with its own dome portion and chamber.

In one embodiment, the cover 14 (or a portion thereof) may be formed from a transparent material so that the pastes 16 and 18 are visible, or so that indicia printed or otherwise disposed under the cover 14 (e.g., on the upper surface of the base plate 20) is visible through the cover 14. Alternatively, the cover 14 and/or base plate 20 may be formed from a material having opaque characteristics, or from a material which either permits or restricts the transmission of selected radiation wavelengths therethrough.

The device 10 is provided from its manufacturer in the form illustrated in FIGS. 1 and 2 for use. The device 10 thus represents a package which includes pastes 16 and 18 for preparation of a single dose of a hardenable dental composition. The pastes are sealed and protected within that package until such time as their combination is desired. The dome portions 48 and 50 are rigid enough to maintain their shape (and spacing from the pastes thereunder) under normal handling conditions. All or a portion of the bottom surface 40 of the cover 14 may be coated with a paste release material so that if the dome portion is inadvertently deformed into contact with the paste thereunder, no paste adheres to it.

Figure 3:
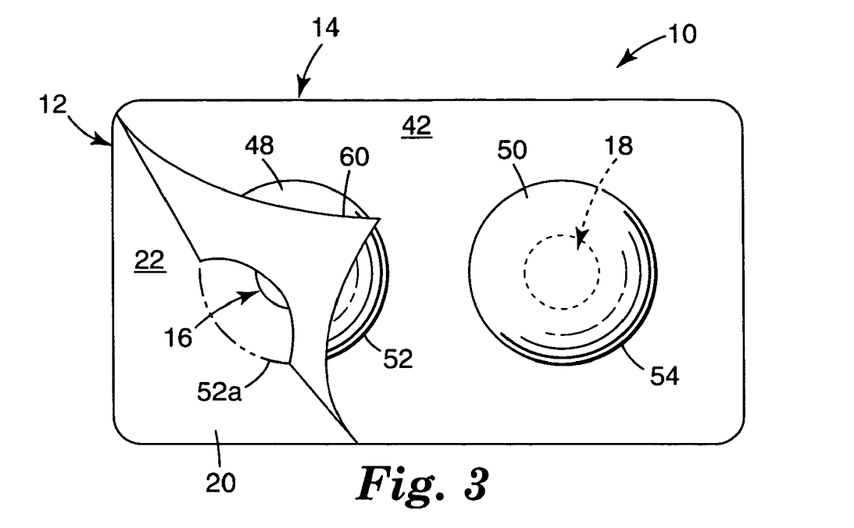
FIGS. 3 and 4 are sequential illustrations of the opening of the delivery device of FIG. 1, illustrating the separation of a top cover from a base plate, and the consequent exposure of the dental pastes affixed on the base plate.
Figure 4:
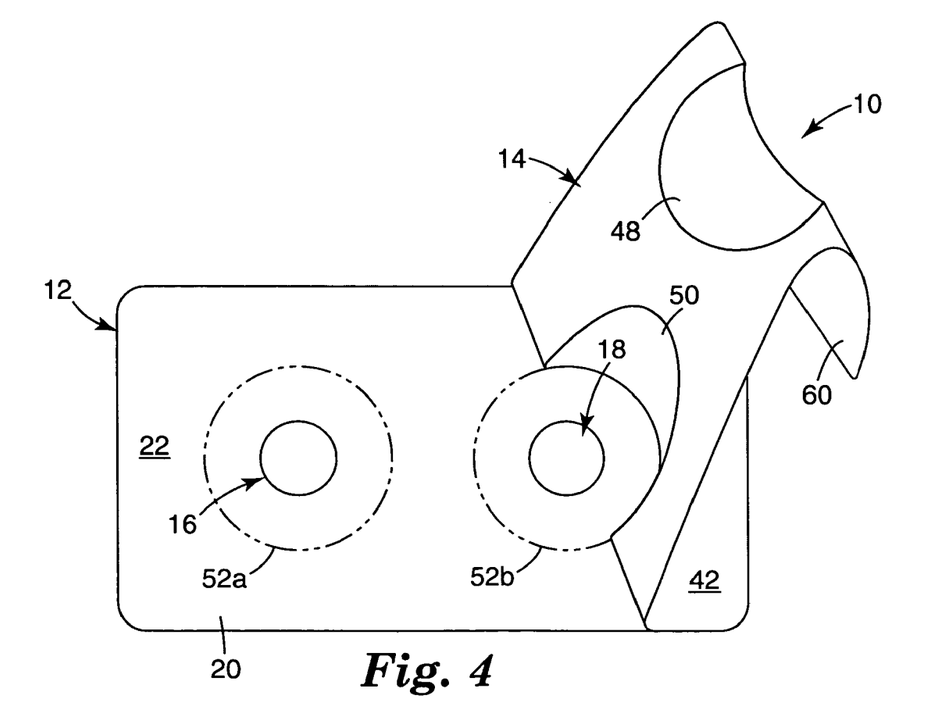
Figure 5:
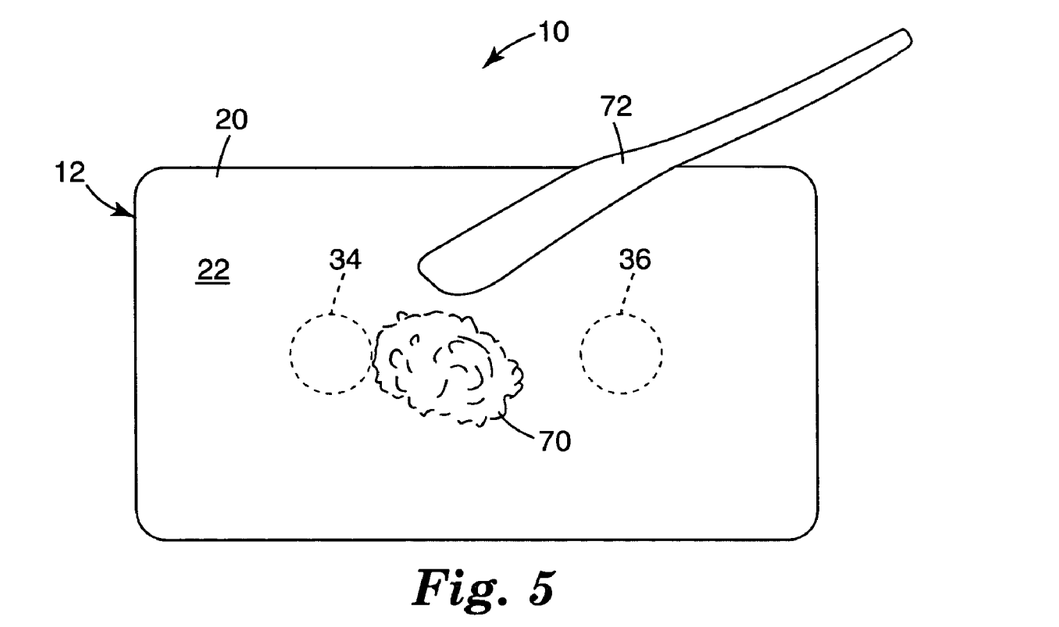
FIG. 5 is a top plan view of the dental pastes being mixed on the base plate.

As illustrated in FIGS. 3 and 4, the cover 14 may be readily separated from the base plate 20 for access to the first and second pastes 16 and 18 by breaking the seal lines 52 and 54. The delivery device may be placed on a surface such as a countertop, with the lower surface 24 of the base plate 20 facing down and the upper surface 22 facing up. The delivery device 10 is held down while one corner 60 or end of the cover 14 is pulled up and away from the upper surface 22 of the base plate 20 to reveal the pastes 16 and 18. The exposed pastes 16 and 18 are then mixed together, either while holding the base plate in one hand or by holding the base plate down on the countertop to form (in combination) a hardenable dental composition 70. The upper surface 22 thus serves as a paste mixing surface, is generally planar and includes the first and second paste areas 34 and 36 (shown in phantom in FIG. 5). The mixing of the pastes 16 and 18 may be performed by any suitable manual or mechanical means, such as by manipulation of a spatula or paddle 72 to provide sufficient applied forces to spread the pastes across the upper surface 22 and mix them together thereon. Once the pastes 16 and 18 are fully mixed to form the hardenable dental composition 70, the composition may then be transferred directly to the patient's tooth, placed into a dispensing capsule or further processed, as desired. In one form, the mixed pastes may cure simply by chemical reactions resulting from the mixture as a self-curing dental composition while in another form, the paste materials when mixed react together for curing and are then further cured by exposure to light.

The packaging, dispensing and mixing arrangement of the present invention is designed for use with paste materials having non-self-leveling material properties. When a material is described herein as "non-self-leveling" or having "non-self-leveling" material properties, that means that, at temperatures of less than about 45° C., the material exhibits no significant flow or mobility under the force of gravity and no significant flow or mobility under the absence of an applied force and, at ambient temperatures of about 15° C. to about 30° C., the material is capable of flow when subjected to a sufficient applied force. The applied force may be imparted by manual manipulation (e.g., by use of a spatula 72 to move the pastes 16 and 18 across the upper surface 22 of the base plate 20 and knead and mix them together) or by mechanical manipulation.

Only those pastes exhibiting the combination of characteristics mentioned above are suitable for use in the inventive device and method. Pastes that flow under an applied force can be readily delivered in precisely controlled amounts to the prescribed locations (e.g., paste areas 34 and 36) on the delivery device (e.g., upper surface 22 of base plate 20) by a variety of well known manufacturing processes. After the application of the pastes to the delivery device, each paste no longer flows and the pastes can subsequently be covered by the domed portion of the cover of the delivery device without the cover contacting the pastes. Each paste is sufficiently high in viscosity that it does not flow, slump or run within its respective chamber and therefore remains essentially free of contact with the cover which serves to protect it. Inadvertent heating to less than about 45° C. and limited shaking or vibrations should not induce significant paste movement or self-leveling of the paste in the absence of an applied force. Removal of the protecting cover yields two or more independent and fully intact paste materials that can be readily rendered flowable with an applied force and subsequently manipulated and mixed to obtain a homogeneous mixture. For example, one can impart thorough mixing of the pastes utilizing a hand held mixing element such as a metal or plastic spatula, wooden or plastic sticks and the like. Alternatively, one could utilize some type of a mechanical stirring or mixing device to induce flow and mixing as well. Pastes that exhibit flow under the force of gravity or in the absence of an applied force are not suitable because they do not remain localized within the domed portion of the cover. Such a paste would undesirably move as soon as its cover was removed, and portions of that paste might remain on that removed cover and thus be unavailable for mixture. Alternatively, pastes that do not exhibit sufficient flow in the presence and absence of an applied force are also not suitable because they can not be readily mixed by hand manipulation on the base of the delivery device.

Pastes such as those described herein are useful for curable dental compositions requiring two or more components to obtain the desired properties. For example, dental materials that are unstable or exhibit a poor shelf life when prepared as a single component system benefit from being prepared in multiple- part dental paste compositions. Combining and mixing such pastes results in one or more chemical reactions that ultimately result in a cured or hardened dental composition suitable for temporary or permanent usage in the oral environment. Accordingly, the amount (volume or mass) of one paste to be mixed is determined as a function of the amount of the other paste (or pastes) of the mixture. Such combined, mixed and cured pastes are used to prepare hardened compositions for a variety of dental restorative applications for the restoration of compromised dentin and enamel tooth structure. Dental applications for these materials include restorative filling materials core build-up materials, permanent and temporary crowns, bridges, inlays, onlays and veneers.

As noted above, such multiple-part dental paste compositions are self-cured (i.e., polymerized or hardened) by one or more chemical reactions upon mixing of the reactive pastes together. Generally, the pastes are comprised of a polymerizable resin, one or more reactive and/or non-reactive fillers and usually a polymerization catalyst system.

One class of materials useful for this purpose are categorized as (meth)acrylate (i.e., acrylate and methacrylate) composites, which are comprised of ethylenically unsaturated compounds (polymerizable resin) that are capable of polymerization in the presence of free radicals. The radicals are preferably generated by combining a redox pair comprising an oxidizing agent (such as a peroxide or persulfate compound) with a suitable reducing agent (such as an aromatic amine or an aromatic sulfinate salt). The oxidizing agent and reducing agent are maintained in the separate pastes of the invention (e.g., separate pastes 16 and 18) to provide good shelf life, and are subsequently mixed at the time of use to induce the polymerization or hardening process.

Other classes of suitable paste materials can be categorized as glass ionomer (GI) or resin modified glass ionomer (RMGI) cement materials which are minimally comprised of a polyalkenoic acid, water and an acid reactive filler. The polyalkenoic acid and the acid reactive glass must be maintained in separate pastes prior to mixing to avoid premature hardening. The delivery device of the present invention provides an effective means of storing, transporting, dispensing and mixing stable pastes prior to use. RMGI materials further comprise the elements previously described as (meth)acrylate composites. Thus, the requirement that such reactive paste materials be maintained completely separated prior to mixing is essential. Other reactive multi-paste chemistries are also suitable for use in connection with the present invention and could benefit from the previously described delivery system solution. For example, such other reactive multi-paste chemistries include two-part epoxies, polyurethane, addition and condensation silicones and the like.

The preparation, mixing, hardening, and evaluation of specific paste materials useful in the devices of the present invention are described in detail in Ser. No. 10/847,781; (Kangas et al.; filed May 17, 2004, assigned to 3M Innovative Properties Company), the entirety of which is herein incorporated by reference. Briefly, paste-paste compositions are described that are useful in a variety of dental and orthodontic applications. Especially suitable dental materials include hardenable ionomer compositions comprising a polyacid, an acid-reactive filler, at least 10 percent by weight nanofiller or combination of nanofillers each having an average particle size of no more than 200 nanometers, a polymerizable component containing (meth)acrylate functionality, and water. Such hardenable ionomer compositions are prepared in two-part paste-paste formulations in which the paste components are stored separately and then combined and hardened during specific dental or orthodontic applications.

The base 12 and cover 14 of the delivery device 10 must be formed from films or other materials which, when pulled apart, can be separated from one another readily. Foil materials advantageous for this purpose include, for example, polyethylene, modified polyethylene, polypropylene, oriented polypropylene, polycarbonate, polyethylene naphthalate, polyamide, polyethylene terephthalate, polyvinylidene chloride, polyvinyl chloride, ethylene/butylacrylate-copolymer, ethylene-vinyl alcohol, cyclic olefin copolymer, liquid-crystal-polymer, acrylonitrile copolymer, and combinations thereof, and paper/plastic composite films or a polyethylene/paper composite. The film materials may include barrier layers in the form of vapor-deposited metal such as aluminum, and/or ceramic oxides such as those derived from silicon or aluminum. If the paste materials to be stored within the dispensing device are particularly sensitive to light, the use of aluminum deposit film materials or opaque printed film materials may be used. However, colored transparent film materials may also be suitable. If a paste material is to be stored in the delivery device which tends to polymerize under the exclusion of oxygen, a single layer film material or laminated film material without an oxygen-type barrier layer such as aluminum may be used as either or both the base 12 or cover 14. When the paste material takes the form of a resin-modified glass ionomer cement, however, such film materials should form the most efficient possible water vapor barrier. Single-layer film materials such as sealable polyethylene or polypropylene films in an appropriate thickness of between 80 and 1,000 microns or plastic laminate films with additional plastic barrier layers such as polyethylene terephthalate, ethylene-vinyl alcohol, ethylene vinyl acetate, polyamide, cyclic olefin copolymer, polyvinyl chloride, polyvinylidene chloride or thin aluminum or ceramic deposits are suitable.

In one embodiment, the base 12 is comprised of a multi-layer base foil of, from bottom to top, polyethylene terephthalate (80 microns thick), aluminum (9 microns thick), white polyethylene terephthalate (12 microns thick), and polyethylene (50 microns thick). In that embodiment, the cover 14 is comprised of a multi-layer cover foil of, from bottom to top, high density polyethylene (50 microns thick), aluminum (20 microns thick), and oriented polypropylene (18 microns thick). In this film, adhesives are provided between the respective layers. This foil is available from Tscheulin-Rothal GMbH, Teningen, Germany, product no. 33500058244/01/5/04. In the multi-layer foils above, adhesives are also provided between the material layers named above. This type of adhesive connection can be achieved in general by common lamination adhesives (which are usually time solvent or water-based or light curing or two component adhesives) or by extrusion lamination (which is a melted (extruded) plastic film placed hot between the two layers to be connected). Extrusion lamination may be especially suitable for aggressive pastes or materials that tend to delaminate the foil/film composition when using ordinary lamination adhesives. Extrusion lamination may be particularly suitable for use between a polyethylene terephthalate layer and a polyethylene layer, since the polyethylene layer is in direct contact with the potentially aggressive paste. In addition, using extrusion lamination between polyethylene terephthalate and aluminum is appropriate for very aggressive pastes/materials. However, if the pastes are not too aggressive, a lamination adhesive will suffice. In addition, a common lamination adhesive will also suffice on the outer side of the aluminum layer.

The connection of the upper surface 22 of the base plate 20 to the bottom surface 40 of the cover 14 can be achieved by heat sealing or by suitable adhesives. For instance, in the multi-layer foil embodiments described above, the top layer of the base and the bottom layer of the cover are polyethylene, so that the two can be sealed together under an application of heat and pressure over time. No matter what form of sealing arrangement is used to connect the base 12 and cover 14, no significant residue is left because of the seal on the upper surface 22 of the base plate 20 once the cover 14 has been removed from the base 12. For instance, slight discontinuities caused on the upper surface 22 by breaking such a heat seal (e.g., such as seal line seams 52a and 54b in FIGS. 3 and 4) are so small that they do not appreciably lessen the desired planar nature of the upper surface 22.

While both the base and cover are disclosed above as multi-layer constructions, each may be formed from a single layer of material. In either form (single layer or multi-layer), additional layers of materials may be provided, such as additional base layers 56 and 58 illustrated in FIG. 2. Such layers may be comprised of reinforcing materials, stiffening materials or other materials to provide additive characteristics to the base 12. In one embodiment, layer 56 is a repositionable pressure sensitive adhesive and layer 58 is a liner therefor. In some applications, it may be desirable for the exposed bottommost surface of the base 12 to have enhanced friction characteristics (such as an exposed adhesive or to present a material having a high coefficient of friction).

The delivery device of the present invention allows for precise amounts of dental pastes to be stored and kept separated. It provides the dentist a controlled ratio of pastes to be mixed together. In dentistry, small amounts of separate pastes are used (e.g., 0.05 grams to 0.9 grams) and the ratio of the combination of such pastes becomes critical for optimum product performance to prepare a final mixed and hardenable dental composition (of, for example, a final mixture of 0.10 grams to 1.8 grams when two pastes are combined). The use of the present invention eliminates error in the measuring out of the optimum ratio of separate paste materials for combination by the dentist. The cover has semi-rigid formed features to cover and protect the paste materials without contact with the materials being stored thereunder. One means for forming the domed portion on the cover is by typical deep-drawing techniques for polymer materials and metallic foils. The base plate of the delivery device becomes the mixing pad for the separate paste materials being mixed, thus eliminating the need to transfer those materials or the problems inherent with an incomplete transfer of all of such materials from their storage containers to a separate mixing area. The delivery device maintains stability of the stored paste materials for prolonged periods of time, and eliminates any possibility of contamination of those materials. The delivery device of the present invention provides ease of use, portability, hygienic delivery, disposable packaging, controlled proportions, low costs, versatility in terms of supporting paste mixtures of two or more separate components with virtually any ratio of relative materials, etc.

In one form, the invention can be characterized as a device for storing and mixing a plurality of dental paste components as described and illustrated herein. In another form, the invention can be characterized as the method of creating a hardenable dental composition as described herein. In yet another form, the invention can be characterized as a method of forming a packaging assembly for storing and dispensing a hardenable dental composition as described and illustrated herein. In each characterization of the invention, the disclosure is not intended to be limited solely to the specifically presented embodiments, but to set forth exemplary embodiments for illustrating and understanding the spirit and scope of the invention.

Figure 6:
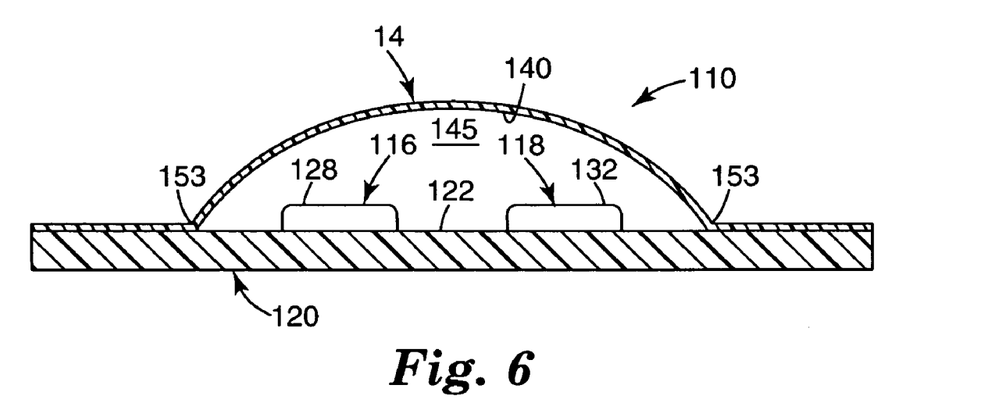
FIG. 6 is a sectional view of an alternative embodiment of the inventive delivery device for storing and mixing a plurality of dental paste components.

An alternative embodiment of the delivery device of the present invention is illustrated in FIG. 6 as delivery device 110. In this embodiment, first and second mixable dental pastes 116 and 118 have compositions which allow their storage within a single chamber 145 defined between a base plate 120 and a dome portion 147 of a cover 114. Except for this change in paste and cover orientation, the delivery device is otherwise the same in characteristics as the delivery device described and illustrated with respect to FIGS. 1-5. For example, the pastes 116 and 118 are non-self-leveling pastes which are maintained in a physically spaced apart manner on an upper surface 122 of the base plate 120, and a bottom surface 140 of the cover 114 is physically spaced apart from any exposed sides 128 and 132 of the first and second pastes 116 and 118, respectively. While there is no hermetic seal between the pastes 116 and 118, there is such a seal about the pastes. In this embodiment, the chamber 145 has an interior volume consisting of the volumes of the first and second pastes 116 and 118 therein and an air volume selected as a function of a composition and volume of at least one of the pastes 116 and 118. The cover 114 is bonded to the upper surface 122 of the base plate 120 at least around the pastes 116 and 118, as at seal line 153.

Figures 7, 8, 9:
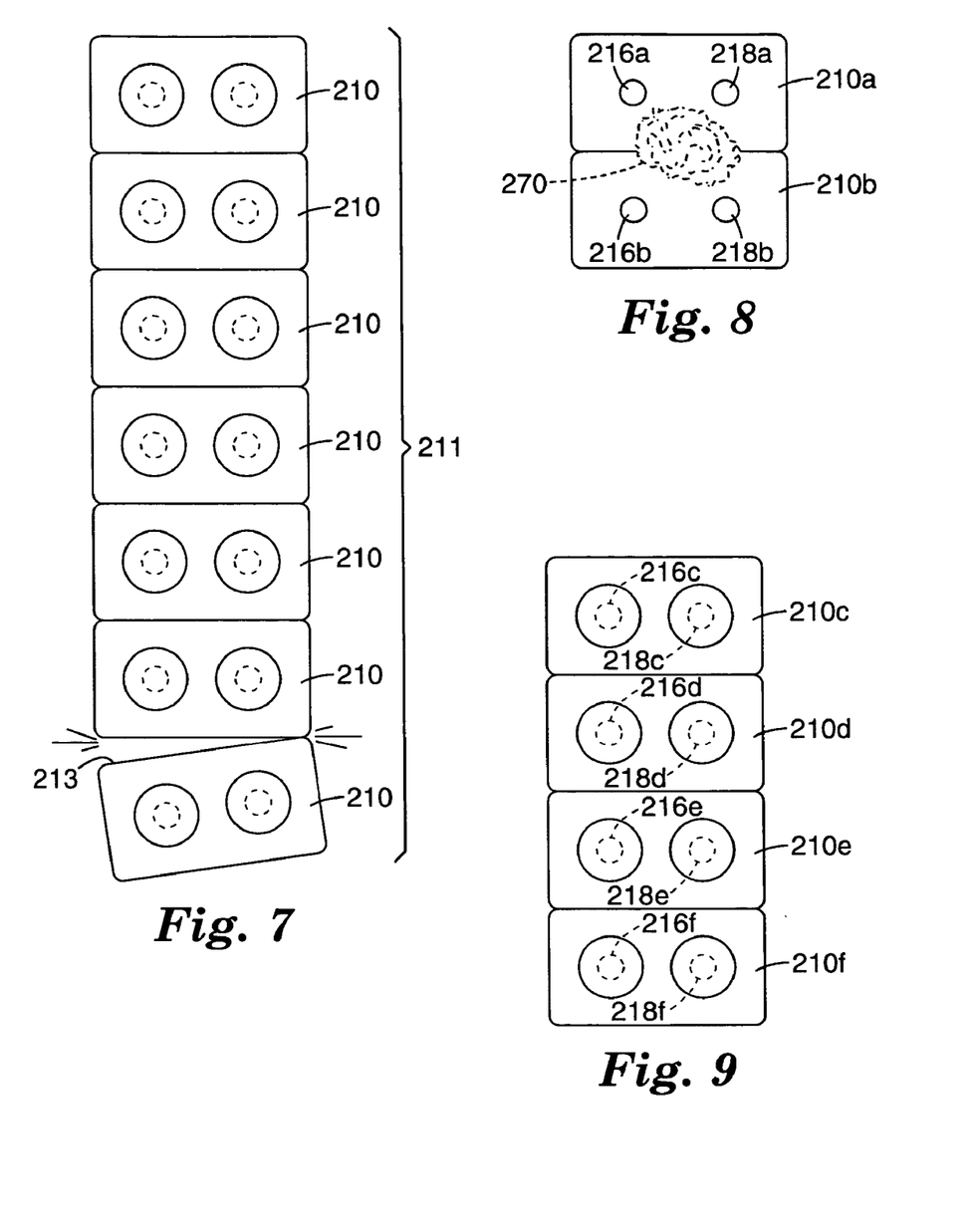
FIG. 7 illustrates a top view of a multiple-unit arrangement including a number of the delivery devices shown in FIGS. 1 and 2.
FIG. 8 illustrates a top view of a pair of adjoining and attached delivery devices, with their covers removed, ready for mixing a double dosage of pastes together.
FIG. 9 illustrates a top view of an alternative embodiment of a multiple-unit arrangement including a number of delivery devices, with their pastes disposed in an alternating format.

A package such as illustrated in FIGS. 1 and 2 or FIG. 6 may be configured to provide a desired unit dosage of hardenable dental composition. Packages may be provided in different sizes for different dosages (such as half sizes or double sizes). However, forming the delivery device in different package sizes causes additional costs for manufacturing and handling. Accordingly, it is advantageous to provide the package in a single size (i.e., dosage) but in a manner in which combining multiple dosages is quite easily accomplished. One means for doing so is illustrated in FIG. 7, where the present invention is in the form of a plurality of unit dose packages 210 formed as a continuous strip 211. Each package 210 may take the form of a delivery device 10 or 110 (or other disclosed variations thereof) which are interconnected for manufacture, transport, delivery and even use. Adjacent packages 210 are separably connected together by a readily frangible connection 213 (shown in phantom between still-joined adjacent packages 210 in FIG. 7). An individual single unit dose package 210 may thus be easily snapped off at the frangible connection 213 for use. In one embodiment, the base plate takes the form of a base plate assembly having a plurality of a juxtapositioned units (i.e., individual base plates) formed therein, with each unit including a respective pair of first and second spaced apart non-self-leveling pastes and respective covers. The units are thus interconnected along tear off or separation lines as at 213.

The frangible connection 213 may take several forms. For instance, since the base plate is relatively thick in order to provide sufficient rigidity for use in mixing, the frangible connection can be obtained by weakening (i.e., notching or scoring) the base plate on its lower surface. Another means for providing the frangible connection is to use laser treatment to partially heat a polymer material beyond its surface. Such a material is generally transparent for the laser but is filled with particles which would absorb the laser light energy (i.e., standard fillers like carbon), thus heating up and causing the polymer chains to break and become brittle within a well defined zone of the material, thereby forming the desired separation line. Other means to generate heat include using light like ultraviolet, infrared or other high frequency heating methods. Further, it may be possible to use chemicals (i.e., solvents or gases) to make certain zones of the base plate brittle by breaking down polymer chains to define the desired separation line. One or more of these material weakening methods may be used separately, or combined.

Alternatively, no pre-defined separation or tear off line may be provided. In that instance, adjacent packages are separated by cutting them apart with a tool, or simply by tearing them apart at a user designated location.

No matter which means is used for creating a weakened line between adjoining packages, the separation or tear off lines at 213 are not evident along the upper surface of a pair of adjoining base plates, however, so as not to interfere with the mixing function of the base plate (i.e., the upper surface of the base plate is planar and without surface discontinuities). Thus, as seen in FIG. 8, two adjoining packages 210a and 210b may be separated from the overall strip 211, the covers of those two adjoining units removed, and then the pastes 216a, 218a, 216b and 218b of those two adjoining packages mixed together simultaneously to define a double dose of the hardenable dental composition (such as hardenable dental composition 270 shown in phantom in FIG. 8). The cover for the packages 210 may be formed from a continuous strip of cover material which is itself perforated or weakened along the frangible connections 213 for separation, or each package 210 may have an individual cover sheet or sheets thereon for the pastes borne by that package. However, the frangible connection 213 creates no discontinuity on or between upper surfaces 222 of bases 212 of those adjoining packages 210a and 210b.

Another means for interconnecting multiple packages for dispensing is to provide separate base plates laminated onto a thin common carrier, where the carrier receives the paste material thereon and defines the mixing surface, and the base plates provide the rigidity required for the mixing process. The carrier can thus be easily torn apart by bending the base plates in opposite directions relative to the mixed surface, or by other suitable separation means. In an alternative embodiment, living hinges may be provided between adjacent packages, with the strip formed so that the hinged-together packages may be stacked in booklet form. Alternatively, the packages may be connected by a connection which is flexible enough to allow winding of the strip on a reel. While FIG. 7 illustrates a single strip of packages, a double wide strip is contemplated. In addition, whether in single strip or double wide strip form, the disposition of the pastes on the packages may be always the same (e.g., first paste 16 on the left and second paste 18 on the right, as viewed in FIG. 1), or the pastes may be disposed from package to package in a laterally alternating format (as illustrated in FIG. 9; e.g., first paste 216c on the left and second paste 218c on the right for package 210c, second paste 218d on the left and first paste 216d on the right for package 210d, first paste 216e on the left and second paste 218e on the right for package 210e, and second paste 218f on the left and first paste 216f on the right for package 210f). As illustrated in FIG. 9, the pastes may be aligned, from package to package in a line longitudinally (top to bottom as viewed in FIG. 9), or they may be disposed in a non-linear arrangement (both longitudinally and/or laterally).

Although the present invention has been described with reference to several embodiments, workers skilled in the art will recognize that changes may be made in form and detail without departing from the spirit and scope of the invention. Accordingly, the invention should not be deemed limited to the specific embodiments described in detail, but instead only by a fair scope of the claims that follow along with their equivalents. For instance, while the disclosure has been directed to dental pastes, the invention has utility in other applications, such as for use in connection with paste components for structural, industrial or consumer adhesives, paste components for composite materials for auto body fillings, and paste components for medical and pharmaceutical materials.

The invention claimed is:

1. A device for storing and mixing a plurality of paste components comprises:
   a base plate having an upper paste mixing surface and a lower surface, the upper mixing surface being planar and having first and second spaced apart paste holding areas thereon;
   a first non-self-leveling paste adhered on the first paste holding area of the upper mixing surface;
   a first cover extending over the first paste area in non-contact relation to the first paste, the first cover removably hermetically sealed to the upper mixing surface around the first paste;
   a second non-self-leveling paste adhered on the second paste holding area of the upper mixing surface; and
   a second cover extending over the second paste area in non-contact relation to the second paste, the second cover removably hermetically sealed to the upper mixing surface around the second paste.

2. The device of claim 1 wherein the first and second covers comprise a continuous layer of cover material.

3. The device of claim 1 wherein the first paste has a first volume and the second paste has a second volume, and wherein the second volume is defined as a function of the first volume.

4. The device of claim 1 wherein the covers are relatively more flexible than the base plate.

5. The device of claim 1 wherein a plurality of juxtapositioned units are formed in the base plate, each unit including a respective pair of first and second non-self-leveling pastes and first and second covers.

6. The device of claim 5 wherein the units are interconnected along tear-off lines.

7. The device of claim 6 wherein each tear-off line comprises a weakened portion between adjacent juxtapositioned units.

8. The device of claim 6 wherein the tear-off lines between units create no discontinuities on the upper mixing surface of the base plate.

9. The device of claim 5 wherein the orientation of the first and second pastes alternates from unit to unit.

10. The device of claim 5 wherein the first paste has a first volume and the second paste has a second volume, wherein, in combination, the volumes of the first and second pastes define a single dosage amount of a hardenable composition, and wherein, in combination, the first and second pastes of two juxtapositioned and connected units comprise a double dosage amount of the hardenable composition.

11. The device of claim 1 wherein the base plate and covers are non-transmissive therethrough with respect to selected radiation wavelengths.

12. The device of claim 1 wherein the covers permit transmission of selected radiation wavelengths therethrough.

13. A device for storing and mixing a plurality of paste components, comprising:
   a base plate having an upper paste mixing surface having first and second spaced apart paste holding areas thereon;
   a first non-self-leveling paste adhered on the first paste holding area, and a second non-self-leveling paste adhered on a second paste holding area; and
   cover extending over the first and second paste areas in non-contact relation to the pastes, the cover being removably hermetically sealed to the upper mixing surface around the first and second pastes to provide a single paste chamber extending over the first and second paste holding areas and their respective pastes.

14. The device of claim 13 wherein the paste chamber has an interior volume consisting of the volumes of the first and second pastes therein and an air volume selected as a function of the composition and volume of at least one of the pastes.

15. The device of claim 1 wherein the first cover comprises a first paste chamber extending over the first paste and wherein the second cover comprises a second paste chamber extending over the second paste.

16. The device of claim 15 wherein the paste chamber has an interior volume which consists of the paste volume for the pastes and an air volume selected as a function of the composition and volume of the pastes.

17. The device of claim 1 and further comprising:
   a stiffening layer in the base plate.

18. The device of claim 1 wherein the lower surface of the base plate has friction enhancing characteristics thereon.

19. The device of claim 18 wherein the friction enhancing characteristics comprise an adhesive.

20. The device of claim 1 wherein the paste components are selected from the group consisting of dental paste components, structural, industrial or consumer adhesive paste components, composite auto body filler material paste components, medical paste components and pharmaceutical paste components.

* * * * *